US00PP22765P2

(12) United States Plant Patent
Silva

(10) Patent No.: US PP22,765 P2
(45) Date of Patent: Jun. 5, 2012

(54) ***CORNUS* PLANT NAMED 'SUMMER GOLD'**

(50) Latin Name: *Cornus kousa*
Varietal Denomination: SUMMER GOLD

(76) Inventor: Crispin Silva, Molalla, OR (US)

( * ) Notice: Subject to any disclaimer, the term of this patent is extended or adjusted under 35 U.S.C. 154(b) by 0 days.

(21) Appl. No.: 12/804,993

(22) Filed: Aug. 3, 2010

(51) Int. Cl.
*A01H 5/00* (2006.01)

(52) U.S. Cl. ..... Plt./220

(58) Field of Classification Search ..... Plt./220
See application file for complete search history.

*Primary Examiner* — June Hwu

(57) ABSTRACT

A new cultivar of *Cornus* plant named 'SUMMER GOLD' whose leaves are variegated mid-green with a prominent wide gold margin and whose variegation persists throughout the summer. In combination these traits set 'SUMMER GOLD' apart from all other existing varieties of *Cornus* known to the inventor.

2 Drawing Sheets

Genus: *CORNUS.*
Species: *kousa.*
Denomination: 'SUMMER GOLD'.

BACKGROUND OF THE INVENTION

The present invention relates to a new and distinct cultivar of *Cornus kousa*, or *kousa* dogwood that is grown for use as a landscape tree. It is known botanically as *Cornus kousa* and will be referred to hereinafter by the cultivar name 'SUMMER GOLD'.

'SUMMER GOLD' arose and was selected by the inventor at the inventor's nursery in Molalla, Oreg., as a chance seedling in a field-grown crop of *Cornus kousa* (species, unpatented) in 2002.

The new *Cornus* variety 'SUMMER GOLD' is an upright tree characterized by variegated foliage. The leaves of 'SUMMER GOLD' are predominantly mid green in color and exhibit a prominent gold margin. The foliage variegation is maintained through the summer.

'SUMMER GOLD' may be compared with the species parent as follows: Whereas the species parent bears non-variegated green leaves, 'SUMMER GOLD' exhibits variegated foliage as described herein.

The closest known comparison varieties known to the breeder are the two variegated cultivars *Cornus kousa* 'Okhan' (unpatented) and the inventor's variety *Cornus kousa* ssp. *chinensis* 'Tri-Splendor' (U.S. Plant Pat. No. 20,008).

When compared with 'Okhan', 'SUMMER GOLD' bears wider and flatter leaves and is more vigorous in its growth and branching.

When compared with 'Tri-Splendor', 'SUMMER GOLD' produces more lateral branches and retains its variegation throughout the summer, whereas 'Tri-Splendor' becomes increasingly non-variegated as summer progresses.

'SUMMER GOLD' was first asexually propagated by the inventor in Molalla, Oreg. in 2005. Asexual propagation was accomplished by grafting 'SUMMER GOLD' onto seedling understock. Since that time, under careful observation, the distinguishing characteristics of 'SUMMER GOLD' have been determined stable and uniform, and are reproduced true to type in successive generations of asexual propagation.

SUMMARY OF THE INVENTION

The following traits have been repeatedly observed and represent the characteristics of the new *Cornus* cultivar 'SUMMER GOLD'. These traits in combination distinguish 'SUMMER GOLD' from all other varieties of *Cornus* known to the inventor. 'SUMMER GOLD' has not been tested under all possible conditions and phenotypic differences may be observed with variations in environmental, climatic and cultural conditions, without however any change in genotype.

1. The leaves of 'SUMMER GOLD' are mid green with a prominent gold margin.
2. The gold margin of the foliage of 'SUMMER GOLD' is approximately 15 mm in width at the widest extremes of a fully expanded leaf.
3. 'SUMMER GOLD' maintains its golden variegation through the summer
4. After one year's growth from initial grafting, 'SUMMER GOLD' is 1.0 meter-1.3 meters in height.
5. A three year old plant of 'SUMMER GOLD' is 2.2 meters-2.5 meters in height.
6. 'SUMMER GOLD' is hardy to USDA Zone 4.

BRIEF DESCRIPTION OF THE DRAWINGS

The accompanying color drawings illustrate the overall appearance of the new *Cornus* variety 'SUMMER GOLD' showing colors as true as it is reasonably possible to obtain in colored reproductions of this type. The specimen used in the drawings is a 2 year old tree which has been grown out of doors in Molalla, Oreg. Colors in the drawings may differ from the color values cited in the detailed botanical description, which accurately describe the actual colors of the new variety 'SUMMER GOLD'.

The drawing labeled

The drawing labeled

Figure 1:
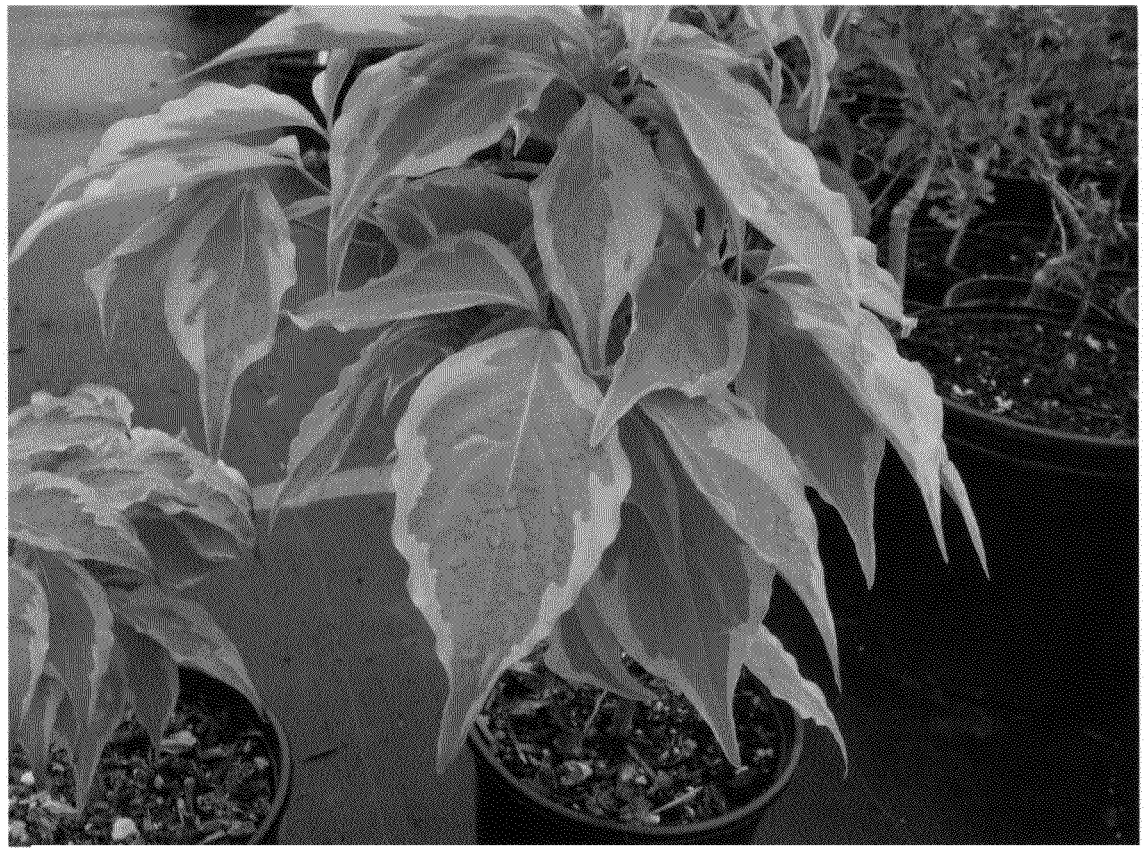
FIG. 1 shows a two year old plant of 'SUMMER GOLD' growing in a 1 gallon container in Molalla, Oreg.
Figure 2:
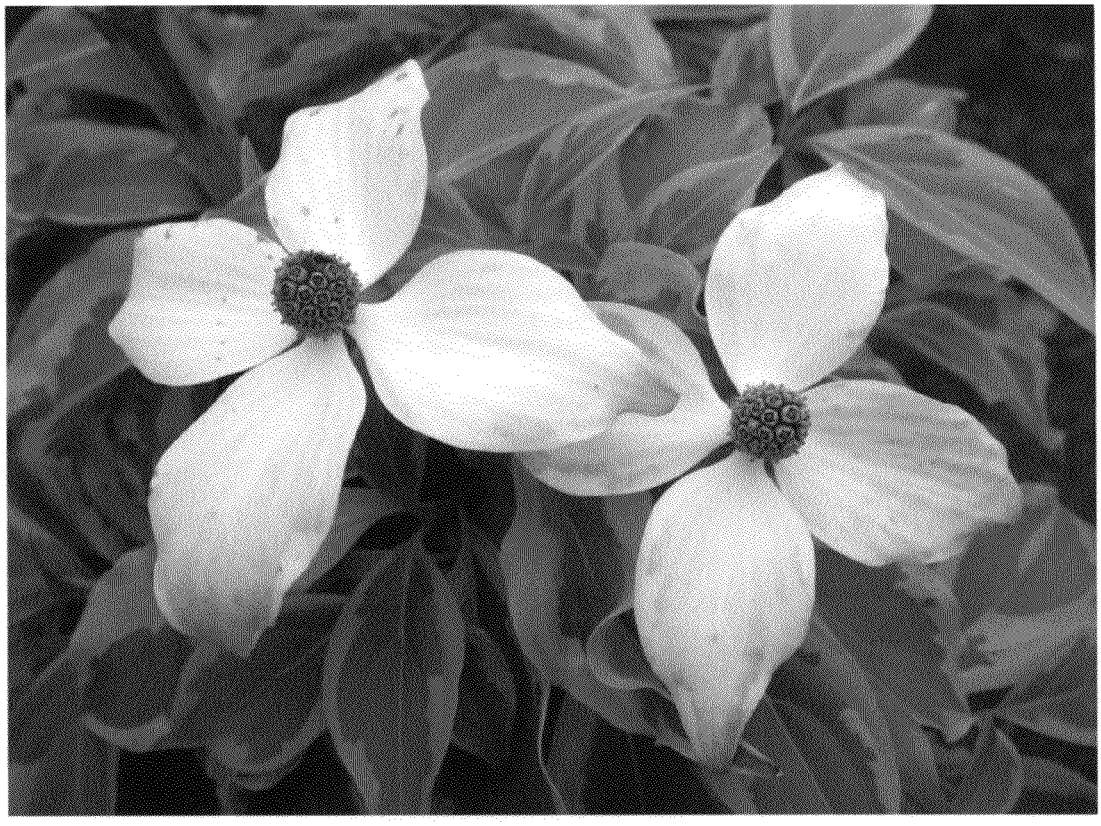
FIG. 2 illustrates the inflorescence and the conspicuous white bracts of 'SUMMER GOLD'. The bracts in this drawing are almost mature having changed from pale green to pure white except for their tips. In addition, two of the depicted bracts exhibit tiny pink spots or circular lesions which would be absent from a totally unblemished inflorescence.

All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'SUMMER GOLD'. Data was collected from a 5 year old plant grown in out of doors in Molalla, Oreg. The color determinations are in accordance with the 5th edition (2007) of The Royal Horticultural Society Colour Chart of The Royal Horticultural Society, London, England, except where general color terms of ordinary dictionary significance are used. No chemicals were used to treat the plants.

Botanical classification: *Cornus.*

Species: *Kousa.*

Common name: *Kousa* dogwood.

Commercial classification: Deciduous flowering tree.

Use: Landscape plant.

Parentage: *Cornus kousa* (species, unpatented).

Plant description:

*Plant habit.*—Upright.

*Plant dimensions* (1 *year*).—1 m-1.3 m in height and 60 cm in width.

*Plant dimensions* (3 *years*).—2.2 m-2.5 m in height and 1 m in width.

*Plant hardiness.*—USDA Zone 4-9.

*Type.*—Deciduous flowering tree.

*Propagation.*—Grafting, budding, or with semi-hardwood cuttings.

*Growth rate.*—Vigorous, faster than other cultivars in the species.

*Cultural requirements.*—Moist soil with good drainage.

*Diseases and pests.*—None known to the inventor.

Branching habit: Ascending.

Angle of emergence: 45 degrees away from the vertical.

Stem:

*Color.*—199A.

*Diameter of trunk at* 10 *cm height.*—9 cm.

*Surface.*—Pubescent.

*Lenticels.*—Sparse, approximately 1 mm-3 mm apart.

*Lenticel size on* 2 *year old branch.*—0.5 mm in length by 0.25 mm in width.

*Lenticel color.*—155A.

Foliage:

*Arrangement.*—Opposite.

*Leaves.*—Division: Simple. Shape: Ovate to elliptic. Dimensions: 40 mm to 90 mm in length and 15 mm to 43 mm in width. Tip: Acuminate. Base: Acute. Venation pattern: Pinnate. Vein color (adaxial surface): Main vein 154D; lateral veins evident only as depressions in the surface, color as adjacent lamina. Vein color (abaxial surface): Main vein 154D; lateral veins evident only as slight ridges in the surface, color as adjacent lamina. Margin: Undulate. Surface (both surfaces): Slightly rough due to the presence of many fine whitish hairs. Leaf color: Ordinarily as described below except lower leaves may exhibit bronzing or reddening which inventor attributes to exposure to cold temperatures. Where present, tips and tip margins of lower leaves exhibit color ranging between 28A to 34A. Immature leaf color (adaxial): Color as leaf emerges: 151A. Color (marginal variegation): 4B when first expanded, becoming darker 12C after one month. Color (leaf center): 145A when first expanded, becoming darker 43C after one month. Immature leaf color (abaxial): Color as leaf emerges: 151A. Marginal variegation: 3D.

Leaf center: 138A and 138B.

*Mature leaf color* (*adaxial*).—Outer margin: 10A. Leaf center: 146B and 35A.

*Mature leaf color* (*abaxial*).—Outer margin: 10C. Leaf center: 148C and 35B.

*Leaf attachment.*—Petiolate.

*Petiole dimensions.*—3 mm in length and 1.5 mm in diameter.

*Petiole surface.*—Rough.

*Petiole color.*—138B.

Inflorescence:

*Form.*—Capitate simple cyme. Flowers single, arranged in hemispheric cluster which is subtended by large showy floral bracts.

*Time and duration of flowering.*—Flowers and bracts develop simultaneously during late May. Bracts persist after anthesis for up to 1 month.

*Flowers.*—Quantity of flowers per inflorescence: 30-35. Dimensions: 4 mm-5 mm in height and width. Calyx: 4-lobed. Petals, 4, separate, 3 mm in length and width, opening pale green becoming creamy-white with 4 separate petals, oblong with rounded apex.

*Floral bracts.*—Fused or unfused: Unfused. Shape: Elliptic to broadly elliptic. Number: 4. Color (both surfaces): Initially pale yellow-green 145C becoming white NN155D from the base and eventually throughout. Surface texture (both): Glabrous. Dimensions: Each bract: 55 mm in length and 22 mm in width. All bracts together (widest point): 10 cm across. Peduncle: 6 cm to 9 cm in length.

*Reproductive organs.*—Stamens: 4, alternate with petals, 1 mm in length, 0.5 mm in diameter. Stamen color: N144B. Anther dimensions: Approximately 1 mm in length and 0.5 mm in width. Anther color: 153C. Pistil: 1, exserted. Style terete, 5 mm in length, 1 mm in diameter, light green in color. Capitate stigma, 1.0-1.5 mm in height and diameter, light brown in color. Fruit: Develops in late August, ripens in late September or October. Sparse, readily eaten by birds and squirrels. Initially held upright on short peduncles which lengthen with the season. Ripe fruit pendulous on peduncles approximately 5 cm in length. Fruit texture and surface: Fleshy drupe with rough surface. Fruit dimensions: 2.5-3.0 mm in diameter. Fruit color: Initially pink, becoming bright raspberry red when ripe. Ovary inferior Seeds, 0-2, irregular shape, mostly ovate 4-5 mm in width, 6-7 mm in length, hard, gray to light tan in color.

What is claimed is:

1. A new and distinct cultivar of *Cornus* plant named 'SUMMER GOLD' as described and illustrated herein.

* * * * *